ular locking member preferably disc shaped snap fitted therewithin. The inner periphery of the locking member is sized and dimensioned to slip over the male luer type connector on one of the fluid flow conduits and to engage an anchor thereon adjacent the root section of the male luer type connector so as to hold the coupling device in assembled position.

United States Patent [19]
Nordgren et al.

[11] Patent Number: 4,676,530
[45] Date of Patent: Jun. 30, 1987

[54] COUPLING ASSEMBLY FOR USE IN FLUID FLOW SYSTEMS

[75] Inventors: Gregory N. Nordgren, West Valley City; Warde M. Cameron, Jr., Sandy, both of Utah

[73] Assignee: Warner-Lambert Company, Morris Plains, N.J.

[21] Appl. No.: 483,050

[22] Filed: Apr. 7, 1983

[51] Int. Cl.4 .............................................. F16L 35/00
[52] U.S. Cl. ..................................... 285/93; 285/332; 285/340; 285/423; 285/901; 285/921; 138/89; 411/521
[58] Field of Search ................. 285/340, 93, 332, 388, 285/432; 411/519, 521, 520; 138/89

[56] References Cited
U.S. PATENT DOCUMENTS

| 2,491,004 | 12/1949 | Graham | 285/340 X |
| 2,739,615 | 3/1956 | Wurzel | 285/340 X |
| 4,059,297 | 11/1977 | Grahl et al. | 285/340 |
| 4,084,843 | 4/1978 | Gassert | 285/340 X |
| 4,133,347 | 1/1979 | Mercer | 285/DIG. 2 |
| 4,266,815 | 5/1981 | Cross | 285/423 X |
| 4,369,781 | 1/1983 | Gilson | 285/332 |

FOREIGN PATENT DOCUMENTS 96207 3/1924 Fed. Rep. of Germany ... 285/DIG. 2
2047831 12/1980 United Kingdom ................ 285/340

OTHER PUBLICATIONS

*Tuff Link* Brochure, Deseret Medical Inc., 5 pages, 1983.
American National Standard for Medical Material-Luer Taper Fittings-Performance, ANS., 18 pages, 1983.

Primary Examiner—Dave W. Arola
Attorney, Agent, or Firm—Louis S. Gillow

[57] ABSTRACT

A press fitted coupling device for fluid flow systems having fluid flow conduits with luer type connectors thereon such as those systems as are used in medical and surgical applications acts to convert a luer type male connector to a male luer lock fitting by means of an internally threaded annular collar having an annular locking member preferably disc shaped snap fitted therewithin. The inner periphery of the locking member is sized and dimensioned to slip over the male luer type connector on one of the fluid flow conduits and to engage an anchor thereon adjacent the root section of the male luer type connector so as to hold the coupling device in assembled position.

5 Claims, 14 Drawing Figures

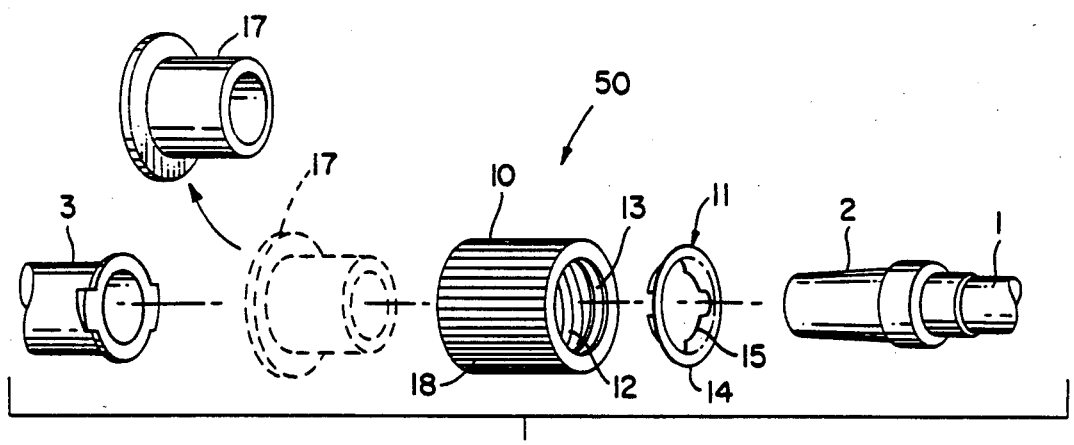
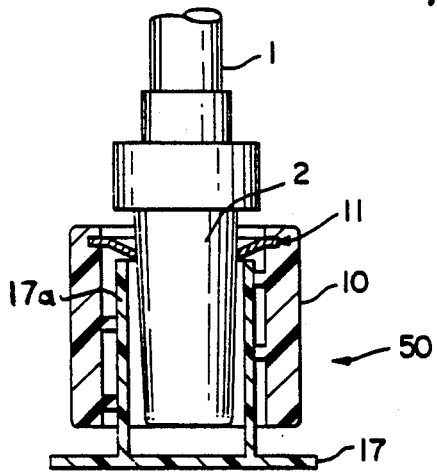
FIG. 2
FIG. 1
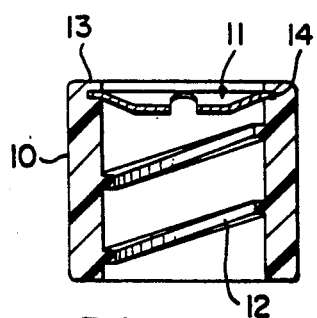
FIG. 3
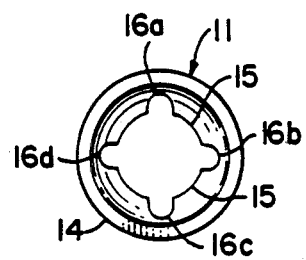
FIG. 4
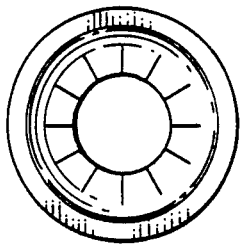 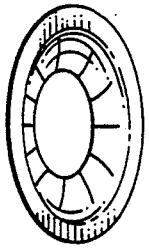
FIG. 5     FIG. 6
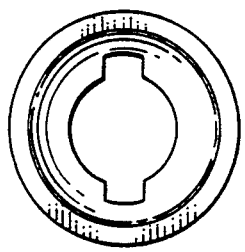 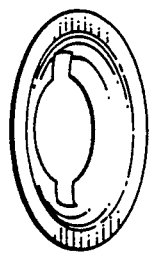
FIG. 7     FIG. 8
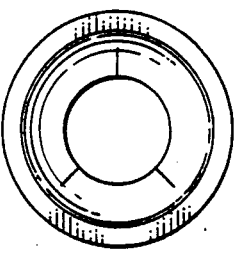
FIG. 9     FIG. 10
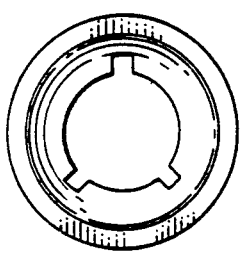 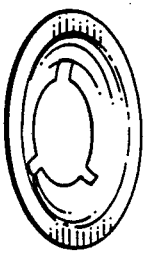 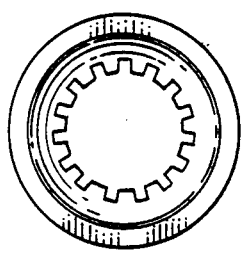 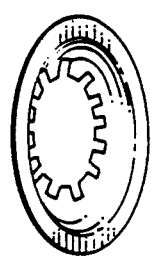
FIG. 11   FIG. 12   FIG. 13   FIG. 14

COUPLING ASSEMBLY FOR USE IN FLUID FLOW SYSTEMS

BACKGROUND OF THE INVENTION

1. Field of the invention

This invention relates generally to coupling devices for fluid flow systems having conduits with luer type connectors thereon, and more particularly to a coupling device adapted to universally convert luer type male slip joint fittings into female fittings and to prevent the disassembly of the coupling device from the luer type male slip joint fitting to which it is connected.

2. Description of the Prior Art

In the medical and surgical field the use of luer type connectors in fluid flow systems having fluid flow conduits made of plastic material which are coupled together or are coupled to in dwelling catheters are common.

The luer type connectors generally consist of a male member having a precise tapered outer surface which matches and mates with a corresponding female member having a similarly tapered bore. The tapered surfaces are so sized that the male member and female member in assembled position effect a slip type interference fit which holds the associated fluid flow conduits in frictional engagement with each other during the use of the fluid flow systems.

The various types of medical and surgical fluid flow systems which use this luer type connector are available on the commercial marketplace and are well known to those skilled in the art.

While these luer type connectors are generally reliable, incidents have occurred where these connections have separated or were inadvertently disconnected from each other. As a consequence, patients may lose blood, or delivery of required or desired medications and other fluids may be interrupted. Such incidents can be life threatening to the critically ill patient, newly born children, and other incapacitated, paralyzed or handicapped patients.

Efforts have been made in the prior art to overcome this problem as is shown in U.S. Pat. Nos. 1,668,315; 3,514,131; 4,052,990; 4,187,848; 4,266,815; 4,270,778, and 4,294,250.

However, many of these devices are either complex and/or expensive and in many instances fail to meet the needs of modern day medicine, which increasingly relies upon disposable accessories and equipment. Disposable accessories and equipment must be available at as low a cost as possible to reduce the medical expenses incurred during the treatment of a given patient.

In view of the shortcomings of fluid conduit connector devices presently available and in use discussed above, a need exists to develop a connector device that offers positive conduit connection at low cost, and which simplifies the use of such devices for the medical community.

SUMMARY OF THE INVENTION

The present invention provides an improved press fittable coupling device connection to a luer type male fitting comprising an annular collar or member internally threaded having a disc type locking washer inserted therein. The washer having a sized opening therethrough so that the annular collar can slide over the luer type male fitting of the associated fluid flow conduit and at the same time be connected by the internally threaded section to the threaded end of a further fluid flow conduit. The washer acts to prevent disassembly of the coupling device from the first fluid flow conduit. Thus a male slip fit luer type male fitting is converted into male luer lock fitting for attachment to a syringe, an in-dwelling catheter, or another conduit as the case may be, thus providing a relatively simple means to insure against the separation of the various elements of the fluid flow system being used on the patient.

The disc member of the present coupling device has an outer periphery which is adapted for snap fittable seating and relatively free rotation in the annular collar adjacent the threaded means thereon. The inner periphery of the disc member defines an opening therethrough having a diameter and configuration such that the annular collar can be pressed over the tapered male connector of the fluid flow conduit. The configuration of the inner periphery operates like a plurality of cutting edges to engage the said tapered male connector so as to prevent easy separation of the coupling assembly therefrom.

The disc member is preferably prepared from a resilient material such as a light weight metal, and by its configuration, is capable of securely engaging male luer connectors that vary in size. In this way the present coupling member offers a universal connecting capability not available in prior coupling devices.

Accordingly it is an object of the present invention to provide an improved coupling device for connecting fluid flow conduits to each other at least one of which has a male luer type slip fitting so as to prevent the accidental separation or disassembly thereof.

It is another object of the present invention to provide an improved coupling device for connecting fluid flow conduits to each other wherein a male luer slip fitting on at least one of said conduits can be converted into a male luer lock fitting.

It is another object of the present invention to provide an improved coupling device for connecting fluid flow conduits to each other which is easy to use and relatively cheap to manufacture.

It is a still further object of the present invention to provide an improved coupling assembly for connecting fluid flow conduits to each other which is made of low cost material and can be disposed of after it has been used.

These as well as other objects and advantages of the present invention will become apparent from the following detailed description taken with the accompanying drawings.

BRIEF DESCRIPTION OF THE DRAWINGS

FIG. 1 is a side elevational view of a fluid flow conduit in a fluid flow system having a tapered male connector at one end thereof to which a coupling assembly including the coupling device in accordance with the present invention is shown in perspective form partly broken away in vertical section.

FIG. 2 is an enlarged exploded perspective view including the coupling device shown in FIG. 1 showing the elements partly broken away in vertical section.

FIG. 3 is an enlarged longitudinal section of the annular collar showing one form of disc type locking member therein.

FIG. 4 is a front end view of the enlarged annular collar shown in FIG. 3.

FIG. 5 is a front view of another form of disc type locking member.

FIG. 6 is a rear perspective view of the disc type locking member shown in FIG. 5.

FIG. 7 is a front view of another form of disc type locking member.

FIG. 8 is a perspective view of the form of disc type locking member shown in FIG. 7.

FIG. 9 is a front view of another form of disc type locking member.

FIG. 10 is a rear perspective view of the form of disc type locking member shown in FIG. 9.

FIG. 11 is a front view of another form of disc type locking member.

FIG. 12 is a rear perspective view of the form of disc type locking member shown in FIG. 11.

FIG. 13 is still another form of disc type locking member.

FIG. 14 is a perspective view of the disc type form of locking member shown in FIG. 13.

DESCRIPTION OF THE ILLUSTRATED EMBODIMENTS

Referring to the drawings FIG. 1 shows one end of a fluid flow conduit 1 in a fluid flow system which has a luer or tapered male slip fit connector 2 thereon to which is connected a press fitted coupling assembly generally designated 50 which is the coupling device of the present invention together with a placement cap device 17.

While the present coupling device is illustrated herein as part of a particular coupling assembly employed in a fluid flow system, it will be understood by those skilled in the art that the coupling device can be connected to any conventional luer or tapered male slip fit connector on any type of equipment, apparatus or accessory as will be clear from the description thereof which will not follow.

Referring to FIGS. 1 and 2, the present coupling device 50 comprises annular collar 10, which has an internally threaded bore as at 12 on the inner wall thereof and is provided with knurling 18 on the outer periphery so as to facilitate manual threading of the annular collar 10 to a correspondingly threaded end of a second female luer fluid flow conduit 3.

When thus assembled, the illustrated annular collar 10 can be moved into tight interference fit engagement with the tapered male connector 2 on the first fluid conduit.

About the inlet end of the internally threaded bore 12 the annular collar 10 has an annular groove as at 13 formed therein in which the outer periphery of the annular disc type locking washer 11 may be snap fitted so as to form a sliding fit between the annular disc type locking washer 11 and the groove 13. Thus, depending on the respective diameters of groove 13 and washer 11, these elements may be relatively rotatable with respect to each other. More particularly the annular collar 10 may rotate independently of the disc type locking washer 11 after the locking washer 11 is fixed onto the tapered male connector 2 of the first fluid coupling 1. Thus, referring to the illustration of the coupling assembly 50, the annular collar 12 is able to draw female luer connector 3 onto the tapered male connector 2 until the tapered surfaces of the male connector 2 and the female luer connector 3 are in interference fit with each other in the conventional fashion for fittings of this type.

The placement cap device 17 is used as a dust cover and also as a depth gauge to assure that the annular collar 12 is axially aligned and the locking disc 13 is engaged on the male luer 2 with sufficient force and that the locking is at a sufficient depth on the male luer so that both a threaded connection and an interference fit with female luer 3 are obtained so as to provide double assurance against fluid leakage and contamination.

The annular disc type locking member 11 may be fabricated from metal or any other material which has sufficient resiliency to permit the coupling device 50 to be assembled on the tapered connector 2, as well as the required strength for preventing the coupling device 50 from separating from the tapered male luer connector 2 after the same is assembled thereon.

In the illustrated form of the coupling device 50, the annular disc type locking washer 11 will have a generally circular outer periphery 14 which will be so sized that it can be snap fitted into the groove 13 on the inner wall of the annular collar 10 as is shown in FIGS. 2, 3 and 4 of the drawings. Additionally the disc shaped locking washer 11 will be shaped so that it forms an arc in cross section or generally a segment of a spherical surface in which the inner periphery 15 is bowed with respect to the outer periphery 14. The inner periphery 15 will define an opening in the disc type locking washer 11 having a diameter or being so sized that the opening will be less than the root diameter of the tapered male connector 2.

As mentioned earlier, the annular disc type locking washer 11 may be mounted rotatably in the groove 13 so that it is transverse to the longitudinal line of the tapered male connector 2 and the bow is facing towards the outlet end of the threaded bore 12 of the annular collar 10. This position permits the coupling device 50 to slide about the tapered male connector 2 during assembly and also to enable the locking washer 11 to be moved longitudinally along the diameter thereof until the edges of the inner periphery as at 15 engage and anchor the coupling device 50 onto the male connector 2.

The edge of the inner periphery 15 can be notched as at 16a, 16b, 16c and 16d for the disc type locking washer 11 illustrated in the preferred form of the invention and shown in FIGS. 2, 3 and 4 of the drawings. This edge may take one of several alternate forms, such as the fluted segments shown in FIGS. 5 and 6, or notched as at FIGS. 7, 8, 11 and 12, segmented as at in FIGS. 9 and 10, or toothed as in FIGS. 13 and 14, so long as the locking member 11 possesses the necessary resilience to engage the tapered male connector 2.

After the disc type locking washer 11 is forced down on a tapered connector 2, back pressure against the fluted segments or notches or teeth causes them to bite deeper into the tapered connector 2 in opposition to any separating force.

It should therefore be apparent that the configurations of the locking washers 11 are particularly capable of assuming a tenacious grip upon the tapered male connector 2 that will prevent any separation of the connector 2 from the present coupling device 50.

In a particular embodiment, the present coupling device may be utilized as part of a coupling assembly to provide an alternate conversion of a male luer fitting to a female threaded lock fitting. Thus, referring to FIGS. 1 to 4 of the drawings the coupling device 50 is shown. Annular collar 10 and a generally disc type locking washer 11 all of which are operatively associated and operatively connected to each other so that in assembled position they can be press fitted onto the luer or tapered male slip fit connector 2 so as not to be readily or easily removed or separated therefrom.

The press fitted coupling assembly including annular collar 10 may be made of any suitable type of plastic or other material which is inert and nonreactive so that it can be used for the objects and purposes of the present invention.

The present coupling device is easily positioned on a male luer fitting such as tapered connector 2 of which will result in the desired formation of a fluidtight, secure connection between the connector 2 of the first conduit and a second conduit, adaptor or other device.

The annular collar 10, with proximately located locking washer 11, is thrust home by seating portion 17a of cap 17, see FIG. 1 upon the end of connector 2 and along the longitudinal axis thereof, until the locking washer 11 is anchored thereon with the placement cap device 17. Since the annular collar 10 is free to rotate relative to the annular disc type locking washer 11 by reason of the groove 13 in which the annular disc type locking washer 11 is mounted, the annular collar 10 can be rotated to thread the female luer lock adaptor 3 tightly onto the threaded section 12, thus drawing the female section 3 of connector 3 into interference fit with the tapered male connector 2.

When the coupling device 50 is mounted upon the male connector or luer fitting 3, the ability of the internally threaded collar 10 to rotate freely thereabout, effectively converts the device 50 into a male luer lock.

Those skilled in the art will readily recognize that an alternate manner of affixing the coupling device 50 in accordance with the present invention would be to first pass the annular collar 10 about the tapered male connector 2 until the annular disc locking washer 11 is set and anchored in assembled position, and then pass the desired female connecting member 3 about the tapered male connector 2 and into threading engagement with the annular collar 10, at which time the annular collar 10 can be rotated to cause the female connecting member 3 to move in a direction to provide the interference fit between the outer surface of the tapered male connector 2 and the corresponding tapered female section of the female connecting member 3.

Thus a relatively simple adaptor comprising a coupling device or coupling assembly has been described which will provide a positive means to prevent the fluid flow conduits or elements of a fluid flow system from disconnecting or disassembling from each other either accidentally or otherwise. This device is inexpensive to manufacture, and thus satisfies the need of contemporary medical and surgical facilities for disposable accessories.

It will be understood that the invention is not to be limited to the specific construction or arrangement of parts shown but that they may be widely modified within the invention defined by the Claims.

What is claimed is:

1. A threaded female luer connector in the form of a collar capable of being rotatably secured to a tapered male luer connector for resistance to axial removal therefrom including:
    a body having an annular collar with an internally threaded bore extending substantially end to end there through to permit said annular collar to be threadedly connected to the locking end of a female connector,
    an annual groove spaced slightly from and inside one end of said annular collar,
    a disc-type annular locking washer being a resilient member having an inner opening and an outer periphery wherein the outer periphery is positioned by a snap fit into said annular groove with said inner periphery provided with edges having a diameter less than a part of the tapered male luer and designed to resiliently engage a tapered male luer connector longitudinally thrust to the part until said edges engage and anchor the longitudinal relationship between the male connector and said annular collar while permitting rotary movement between said locking washer outer periphery and said annular groove of said collar said disc-type annular locking washer being the sole engagement means between said collar and the tapered male luer connector.

2. The annular collar of claim 1 wherein said locking washer inner periphery is longitudinally extended away from the plane of said washer when said washer is positioned in said annular groove whereby said longitudinally extended inner periphery is axially inward of said annular collar.

3. The annular collar of claim 2 wherein a cap is provided to cover the end opposite said annular groove of said annular collar to seat within the space between said annular collar and the tapered end of the male connector.

4. The annular collar of claim 3 wherein said cap having a seating portion extending into the space sufficiently to act axially against said locking washer about said inner periphery is used as a dust cover and also as a depth gauge to thrust home said locking washer so that said collar is axially aligned and that said locking washer is engaged upon the tapered end of the male connector with sufficient force and at a sufficient longitudinal depth to provide a secure, rotatable female threaded connection for drawing a female luer into interference fit with the tapered end of the male connector preventing fluid leakage there between.

5. A threaded female luer connector in the form of a collar capable of being rotatably secured to a tapered male luer connector for resistance to axial removal therefrom including:
    An annular collar made of a plastic material with an internally threaded bore extending substantially end to end therethrough to permit said annular collar to be threadedly connected to the locking end of a connector,
    an annular groove spaced slightly from and inside one end of said annular collar,
    a disc-type annular locking washer being a resilient member having an inner opening and an outer periphery wherein the outer periphery is positioned by a snap fit into said annular groove and said inner opening periphery has a diameter less than at least a portion of the male luer and a plurality of spaced notches and is designed to resiliently deform to the diameter of the portion of the male luer and thereby engage the tapered male luer connector longitudinally thrust therethrough to lock the longitudinal axial relationship between the male connector and said annular collar while permitting rotary movement between said locking washer outer periphery and said annular groove of said collar, said disc-type annular locking washer being the sole engagement means between said collar and the tapered male luer connector.

said locking washer inner periphery being longitudinally extending away from the plane of said washer in the direction of insertion of the male luer connector when said washer is in said groove, a cap to cover the end opposite said groove and seat within the space between said collar and male luer, and a seating portion on said cap extending into said space to use as a depth gauge for proper engagement of said inner periphery upon said male luer during assembly of said collar to said luer with sufficient force and depth so both a threaded connection and an interference fit with a female luer are obtained.

* * * * *